US00PP33565P2

(12) United States Plant Patent
Mathey

(10) Patent No.: US PP33,565 P2
(45) Date of Patent: Oct. 19, 2021

(54) ***BUDDLEIA* PLANT NAMED 'SMNBDB'**

(50) Latin Name: *Buddleia davidii*
Varietal Denomination: SMNBDB

(71) Applicant: Megan M. Mathey, Holland, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 17/039,831

(22) Filed: Sep. 30, 2020

(51) Int. Cl.
*A01H 5/02* (2018.01)

(52) U.S. Cl.
USPC ..... Plt./242

(58) Field of Classification Search
USPC ..... Plt./242
See application file for complete search history.

*Primary Examiner* — Annette H Para
(74) *Attorney, Agent, or Firm* — C. Anne Whealy

(57) ABSTRACT

A new and distinct cultivar of *Buddleia* plant named 'SMNBDB', characterized by its compact, upright and outwardly spreading plant habit; vigorous growth habit; freely branching habit; dense and bushy appearance; leathery and durable leaves; freely flowering habit; large and dense conical inflorescences with numerous strong reddish purple-colored flowers; and good garden performance and winter hardiness.

2 Drawing Sheets

Figure 1:
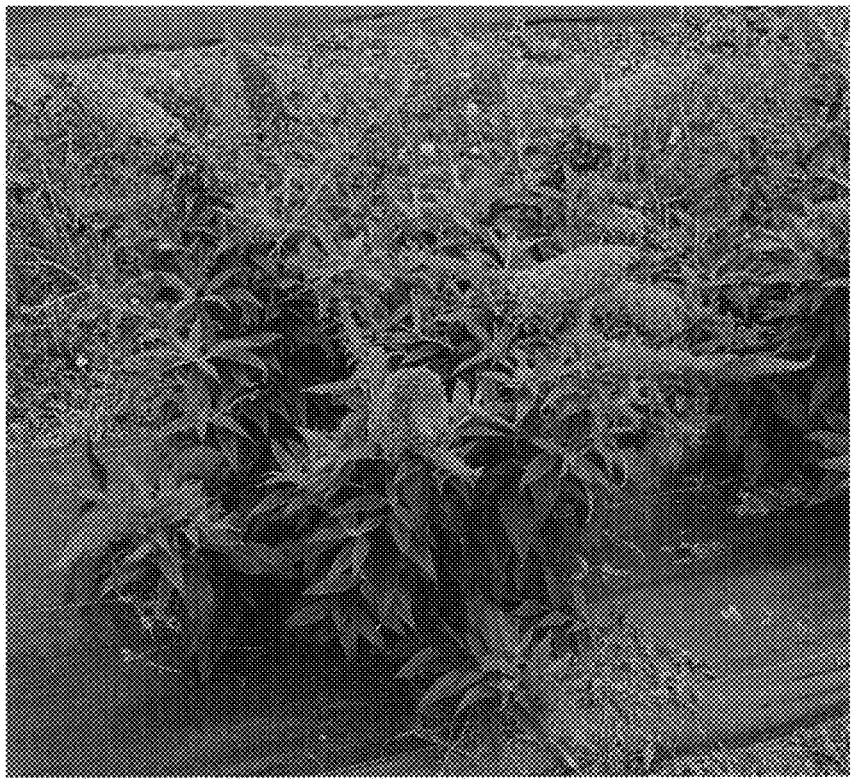

Botanical designation: *Buddleia davidii.*
Cultivar denomination: 'SMNBDB'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Buddleia* plant, botanically known as *Buddleia davidii* and hereinafter referred to by the name 'SMNBDB'.

The new *Buddleia* plant is a product of a planned breeding program conducted by the Inventor in Grand Haven, Mich. The objective of the breeding program was to create new *Buddleia* plants with strong branches and attractive plant form and flower coloration.

The new *Buddleia* plant originated from a cross-pollination conducted by the Inventor in June, 2015 in Grand Haven, Mich. of *Buddleja hybrida* 'Miss Molly', disclosed in U.S. Plant Pat. No. 23,425, as the female, or seed, parent with *Buddleia davidii* 'SMNBDPT', disclosed in U.S. Plant Pat. No. 28,836, as the male, or pollen, parent. The new *Buddleia* plant was discovered and selected by the Inventor as a single flowering plant within the progeny of the stated cross-pollination in a controlled environment in Grand Haven, Mich. during the summer of 2017.

Asexual reproduction of the new *Buddleia* plant by softwood stem cuttings in a controlled environment in Grand Haven, Mich. since the summer of 2017 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNBDB'. These characteristics in combination distinguish 'SMNBDB' as a new and distinct *Buddleia* plant:

1. Compact, upright and outwardly spreading plant habit.
2. Vigorous growth habit.
3. Freely branching habit; dense and bushy appearance.
4. Leathery and durable leaves.
5. Freely flowering habit.
6. Large and dense conical inflorescences with numerous strong reddish purple-colored flowers.
7. Good garden performance and winter hardiness.

Plants of the new *Buddleia* differ primarily from plants of the female parent, 'Miss Molly', in the following characteristics:

1. Plants of the new *Buddleia* are more compact than plants of 'Miss Molly'.
2. Plants of the new *Buddleia* have larger inflorescences than plants of 'Miss Molly'.
3. Plants of the new *Buddleia* and 'Miss Molly' differ in flower color as plants of the *Buddleia* have strong reddish purple-colored flowers whereas plants of 'Miss Molly' have purplish red-colored flowers.

Plants of the new *Buddleia* differ primarily from plants of the male parent, 'SMNBDPT', in the following characteristics:

1. Plants of the new *Buddleia* have larger inflorescences than plants of 'SMNBDPT'.
2. Plants of the new *Buddleia* and 'SMNBDPT' differ in flower color as plants of the *Buddleia* have strong reddish purple-colored flowers whereas plants of 'SMNBDPT' have light purple-colored flowers.

Plants of the new *Buddleia* can also be compared to plants of *Buddleia davidii* 'SMNBDO', disclosed in U.S. Plant Pat. No. 28,796. In side-by-side comparisons, plants of the new *Buddleia* differ primarily from plants of 'SMNBDO' in inflorescence size as plants of the new *Buddleia* have larger inflorescences than plants of 'SMNBDO'. In addition, flower of plants of the new *Buddleia* are more pink in color than and not as purple in color as flowers of plants of 'SMNBDO'.

BRIEF DESCRIPTION OF THE PHOTOGRAPHS

The accompanying colored photographs illustrate the overall appearance of the new *Buddleia* plant showing the colors as true as it is reasonably possible to obtain in colored reproductions of this type. Colors in the photographs may differ slightly from the color values cited in the detailed botanical description which accurately describe the colors of the new *Buddleia* plant.

The photograph on the first sheet (FIG. 1) is a side perspective view of a typical flowering plant of 'SMNBDB' grown in an outdoor nursery.

Figure 2:
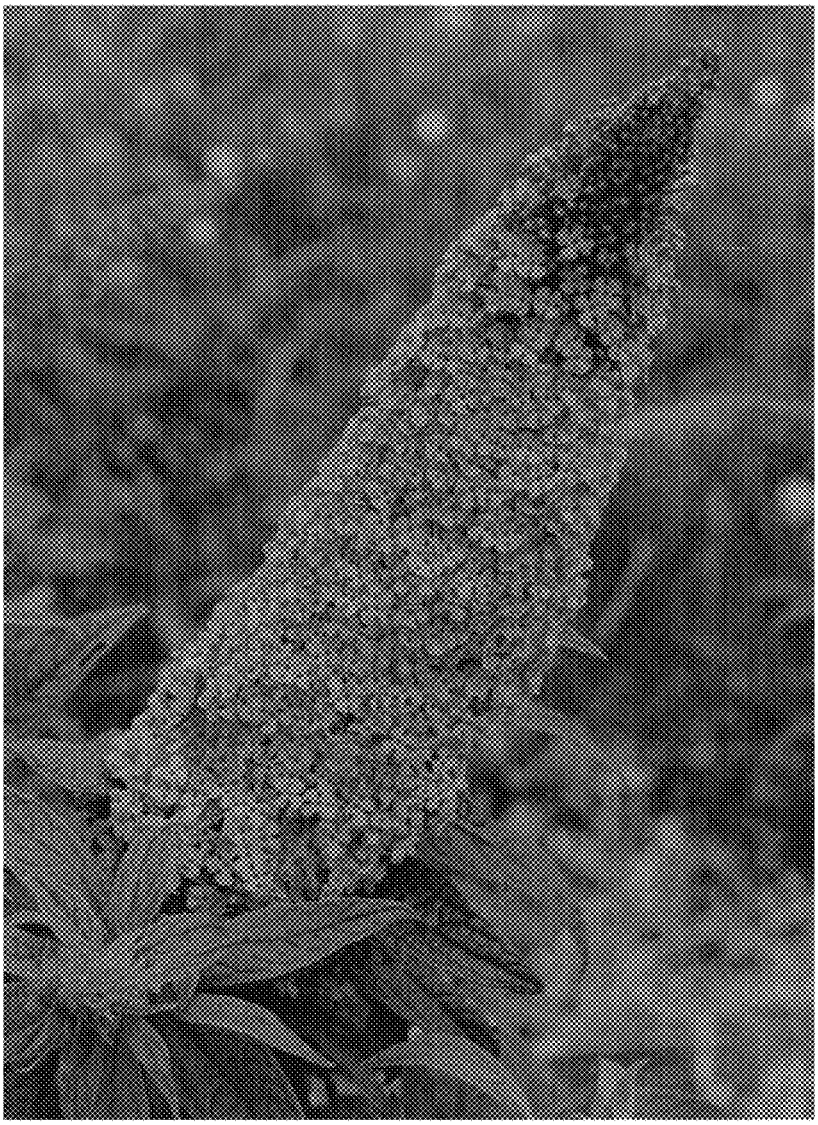

The photograph on the second sheet (FIG. 2) is a close-up view of a typical inflorescence and leaves of a plant of 'SMNBDB'.

DETAILED BOTANICAL DESCRIPTION

The following observations, measurements and values describe plants grown during the mid to late summer in three-gallon containers in a polyethylene-covered greenhouses in Grand Haven, Mich. and under cultural practices typical of commercial *Buddleia* production. Plants were two years old when the photographs and description were taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Buddleia davidii* 'SMNBDB'.

Parentage:

*Female, or seed, parent.*—*Buddleja hybrida* 'Miss Molly', disclosed in U.S. Plant Pat. No. 23,425.

*Male, or pollen, parent.*—*Buddleia davidii* 'SMNBDPT', disclosed in U.S. Plant Pat. No. 28,836.

Propagation:

*Type*.—By softwood stein cuttings.

*Time to initiate roots plant, summer*.—About two weeks at temperatures about 25° C.

*Time to produce a rooted plant, summer*.—About 40 days at temperatures about 25° C.

*Root description*.—Fine, fibrous; typically tan in color, actual color of the roots is dependent on substrate composition, water quality, fertilizer, substrate temperature and physiological age of roots.

*Rooting habit*.—Freely branching; dense.

Plant description:

*Plant and growth habit*.—Deciduous perennial shrub; compact, upright and outwardly spreading plant habit; rounded appearance; relatively short internodes; dense and bushy appearance; vigorous growth habit and moderate growth rate.

*Plant height*.—About 48 cm.

*Plant width* (*spread*).—About 78 cm.

*Lateral branches*.—Quantity: Freely branching habit with about six to ten primary lateral branches developing per plant. Length: About 43 cm. Diameter: About 8 mm. Internode length: About 3 cm. Strength: Strong. Aspect: Upright to about 45° from vertical. Texture: Initially, pubescent, then becoming glabrous and woody with development. Color, developing: Close to 146D. Color, woody: Close to 195B.

Leaf description:

*Arrangement and appearance*.—Opposite, simple.

*Length*.—About 13.5 cm.

*Width*.—About 4 cm.

*Shape*.—Lanceolate.

*Apex*.—Acute to acuminate.

*Base*.—Cuneate.

*Margin*.—Slightly serrate.

*Texture, upper surface*.—Developing leaves are pubescent; with development, smooth, glabrous, coriaceous.

*Texture, lower surface*.—Pubescent, venation prominent; coriaceous.

*Venation pattern*.—Pinnate.

*Color*.—Developing leaves, upper surface: Close to 143A. Developing leaves, lower surface: Close to 194C. Fully expanded leaves, upper surface: Close to 147A; venation, close to N144A. Fully expanded leaves, lower surface: Close to 194C; venation, close to 193A.

*Petioles*.—Length: About 7 mm. Diameter: About 3 mm. Texture, upper and lower surfaces: Pubescent. Color, upper surface: Close to 146C. Color, lower surface: Close to 147D.

Flower description:

*Flower type and flowering habit*.—Single salverform flowers arranged on terminal panicles; inflorescences face mostly outwardly; panicles long and conical in shape; freely flowering habit with more than 100 flowers developing per inflorescence and more than 1,000 flowers developing per plant during the flowering season; flowers face upright to outwardly depending on position on the panicle; flowers persistent.

*Fragrance*.—Fragrant; sweet, honey-like, pleasant.

*Natural flowering season*.—Long flowering period, plants flower continuously from mid-summer into the early autumn in Michigan.

*Flower buds*.—Height: About 1 cm. Diameter: About 2 mm. Shape: Lanceolate. Color: Proximally, close to 70B and distally, close to 70A.

*Inflorescence length*.—About 12 cm.

*Inflorescence diameter*.—About 4 cm.

*Flower diameter*.—About 5 mm.

*Flower depth* (*height*).—About 8 mm to 10 mm.

*Throat diameter*.—About 1 mm.

*Tube length*.—About 6 mm.

*Tube diameter, proximally*.—About 1 mm.

*Petals*.—Quantity per flower: Typically four in a single whorl fused at the base. Length: About 3 mm. Width: About 4 mm. Shape: Oblong to obovate. Apex:

Obtuse. Margin: Entire; slightly undulate. Texture, upper and lower surfaces: Smooth, glabrous; soft. Color: Developing petals, upper and lower surfaces: Close to N78B. Fully developed petals, upper and lower surfaces: Close to N78B; color becoming closer to 86A with development. Throat: Close to 15A. Tube: Close to 64B.

*Sepals*.—Quantity per flower: Typically four in a single whorl. Length: About 1 mm. Width: Less than 1 mm. Shape: Lanceolate to ovate. Apex: Acute. Base: Cuneate. Margin: Entire. Texture, upper and lower surfaces: Slightly pubescent. Color, upper surface: Proximally, close to 145C and distally, close to 143A. Color, lower surface: Close to 145B.

*Peduncles*.—Length: About 7 mm. Diameter: About 1 mm. Strength: Strong. Angle: Upright to outwardly; about 15° to 80° from vertical. Texture: Pubescent. Color: Close to 144B.

*Pedicels*.—Length: About 2 mm. Diameter: About 1 mm. Strength: Strong. Angle: About 45° from vertical. Texture: Pubescent. Color: Close to 144B.

*Reproductive organs*.—Stamens: Quantity per flower: Typically four. Filament length: About 0.5 mm. Filament color: Close to 26A. Anther length: About 1 mm. Anther shape: Oblong. Anther color: Close to 155B. Pollen amount: Scarce. Pollen color: Close to 11C. Pistils: Quantity per flower: One. Pistil length: About 1 mm. Stigma shape: Oblong. Stigma color: Close to 144B.

*Seeds and fruits*.—To date, seed and fruit development have not been observed on plants of the new *Buddleia*.

Pathogen & pest resistance: To date, plants of the new *Buddleia* have not been observed to be resistant to pathogens and pests common to *Buddleia* plants.

Garden performance: Plants of the new *Buddleia* have been observed to have good garden performance and tolerate rain, wind and to tolerate temperatures ranging from about −31° C. to about 38° C.

It is claimed:

1. A new and distinct *Buddleia* plant named 'SMNBDB' as illustrated and described.

* * * * *